United States Patent [19]

Bircumshaw

[11] Patent Number: 4,939,965

[45] Date of Patent: Jul. 10, 1990

[54] CUTTING AND THE LIKE TOOLS

[75] Inventor: Peter Bircumshaw, Sprotborough, England

[73] Assignee: W. E. McKenzie Limited, Grimsby, England

[21] Appl. No.: 243,807

[22] Filed: Sep. 13, 1988

[30] Foreign Application Priority Data

Sep. 18, 1987 [GB] United Kingdom ................. 8721974
Nov. 27, 1987 [GB] United Kingdom ................. 8727825

[51] Int. Cl.$^5$ .............................................. B23B 5/00
[52] U.S. Cl. ........................................ 82/113; 82/128
[58] Field of Search .................. 82/1.1, 1.2, 4 R, 4 C, 82/52, 53, 901, 172, 173, 113, 128

[56] References Cited

U.S. PATENT DOCUMENTS

| | | | |
|---|---|---|---|
| 4,085,505 | 4/1978 | McElroy | 30/103 |
| 4,101,368 | 7/1978 | Page | 83/157 |
| 4,186,630 | 2/1980 | Lindhag | 82/4 C |
| 4,532,837 | 8/1985 | Cuchinbury | 82/4 C |
| 4,668,133 | 5/1987 | Cambell | 82/1.2 |
| 4,678,379 | 7/1987 | Sunday | 82/1.2 |
| 4,729,502 | 3/1988 | Fukukawa | 29/33 D |
| 4,758,121 | 7/1988 | Kwech | 82/4 C |

Primary Examiner—Frederick R. Schmidt
Assistant Examiner—Blynn Shideler
Attorney, Agent, or Firm—R. A. Giangiorgi

[57] ABSTRACT

The invention relates to cutting and the like tools and is particularly concerned with the cutting of an internal weld bead from within plastics pipes. It is well-known to remove an external weld bead from the junction between two plastics pipes, not only to provide a smooth external profile but also to allow the weld between the pipes to be inspected. The costs and difficulties in removing the internal beads at the welded junction has frequently resulted in the internal bead being left, and when the internal weld cannot be inspected, and turbulence created in gas or fluid being driven through the pipeline results in a higher power requirement. One object of the invention is to provide a simple and effective means of removing an internal weld bead, which objective is met by a construction characterized by a body member (1), adjustable support means (23, 28) on the body member to locate the body member within a pipe, a motor (2) with the body member, a feed screw means (7) slidably mounted on shaft (3) extending from the motor, the feed screw means (7) engaging a threaded bore in a drive screw means (8) located in the body member, and there being cutter and the like means (21, 30) removably secured to the end of the feed screw means.

8 Claims, 2 Drawing Sheets

CUTTING AND THE LIKE TOOLS

This invention relates to cutting and the like tools, and is particularly, but not necessarily exclusively, concerned with tools for the effecting of cutting and the like operations internally of plastics pipes.

There is currently the increasing use of plastics pipelines in several industries such as for example the water industry and the gas industry. A most frequently used means of creating a plastics pipeline is to take discrete lengths of plastics pipe, and to butt weld the ends of the plastics pipes together. It is of primary importance particularly to the gas industry that there is no fault in the weld between two adjacent lengths of plastics pipe, and whilst the weld can readily be checked at its external surface there is considerable difficulty in checking the weld internally of the pipes.

It is equally so that by virtue of the butt welding technique both an external and internal bead are formed in the vicinity of the weld. Customarily the external bead is removed and which provides the ability to allow the weld to be inspected, but because of the difficulties of removing an internal bead there is a tendency for the internal bead to be left in place, and it is well-known that the presence of a number of such internal beads along the length of a pipeline results in a higher power requirement to drive gas or fluid along the pipeline than would be so in the absence of the presence of such beads.

It is therefore an object of the present invention to provide a cutting tool capable of removing an internal bead at the joint between two pipe lengths and another object to provide such a cutting tool capable of extracting a cut bead from within a pipe. A still further object is to provide a tool that by simple adaptation can perform other required operations internally of pipes.

According to the present invention, a cutting and the like tool comprises a body member, adjustable support means on the body member to locate the body member within a pipe a motor within the body member, a feed screw means slidably mounted on a shaft extending from the motor, the feed screw means engaging a threaded bore in a drive screw means located in the body member and there being cutter and the like means removably secured to the end of the feed screw means. The motor may be hydraulically, pneumatically, or electrically operable.

Whilst the drive shaft of the motor may be cylindrical, as a means of preventing the feed screw from jamming on the motor shaft, the motor shaft may be tapered to engage in a correspondingly tapered bore in the feed screw, and in either instance, key and keyway means being employed to provide for the positive driving of the feed screw by the motor shaft, whilst permitting the feed screw to slide along the motor shaft.

It is further preferred that three support means are provided equally spaced around the periphery of the body member, at least one of which is adjustable. Adjustment of the support means can be by relatively simple screw means, however to enable the cutting and the like tool to be secured within a pipe at a distance remote from one end, it is preferred that at least one of said support means is hydraulically or pneumatically actuated. Thus, with two skids manually set at a distance from the body to position the longitudinal axis of the motor shaft on the longitudinal axis of the pipe and with the third hydraulically or pneumatically actuate support in a retracted position, the cutting and the like tool can readily be inserted into a pipe and positioned at any required distance along the pipe, and when the third support is activated to bring it into contact with the internal pipe wall with a force sufficient to locate positively the cutting and the like tool at that position along the length of the pipe. It will readily be understood that the adjustable nature of the supports allows the cutting and the like tool to be accurately centred despite any deviations in pipe diameter from a nominal diameter, and equally allows accurate centring across a range of diameters within the limits of adjustability of the support means. The cutting and the like tool can however be readily adapted to suit a different range of pipe diameters simply by removing the support means and replacing them with support means of an appropriate length and degree of adjustability, and in connection with the hydraulically or pneumatically operated support replacing it with one having an appropriate stroke length.

To provide for a cutting or the like action, a cutter support body may be secured to the end of the feed screw means emerging beyond the drive screw, with the cutter support body emerging from the housing. A transverse bar of a length to suit the diameter of the pipe in question may be secured to the end of the cutter support body to project laterally to an equal degree to each side of the cutter support body and there being a cutting or the like tool mounted at at least one, and preferably at each end of the transverse bar. It is highly desirable that each cutting and the like tool is resiliently mounted, and whereby any ovality or other deviation from true circularity of the pipe can be accommodated.

In its form of construction that serves as an internal bead removal tool, each cutting tool is a forwardly projecting cutting blade, both pivotally and resiliently mounted, at the end of the transverse arm, the resilient mounting means (preferably a spring) causing each cutting tool to assume an outwardly divergent position in its operative condition. It is preferred that a means is provided to hold each cutting tool in an inoperative position, to enable the cutting tool to be progressed along a pipe to the position of a bead and when said means are released to allow the cutting blades to spring outwards and into contact with the internal wall of the pipe immediately in front of a bead. Preferably, each cutter blade is mounted on an appropriate holder pivotally located at the end of the transverse arm, and to reduce the frictional effect of the holder sliding around the internal surface of a pipe, it is further prferred that a freely rotatable roller is located on the holder to contact the pipe interior. For accurate positioning of the cutting blades, camera means may be provided on the cutting tool with an attendant monitor screen provided for the operative.

In its bead cutting application, and to enable a cut bead to be removed from the pipe interior, it is preferred to provide a means associated with each cutter blade to hold the cut bead on its removal. Thus, each cutter blade may have a generally U-shaped yoke member e.g. secured to the cutter blade holder.

Thus, on activation of the motor, the feed screw means and hence the cutter holder body and the transverse bar and cutting blades are caused to rotate, and engagement between the feed screw means and the drive screw means causes the feed screw means and hence the cutting blades to move in a direction away from the housing. Consequently, the cutting blades pierce the bead at the junction between the bead and the pipe wall, the rotation and gradual progression of the cutting blades then cutting the bead from the pipe wall, with the advantage that the severed bead is positively held and whereby on retraction of the cutting tool from within the pipe the cut bead is brought out from within the pipe.

In its bead cutting application the cutting tool of the invention provides the major advantage of complete bead removal from a pipe interior in relatively simple manner with the attendant equally major advantage that the cut surface of the bead provides for the immediate inspection of the condition of the weld at the internal surface of the pipe.

Whilst a major application of the cutting tool and the like of the invention is in connection with internal bead removal, it will readily be appreciated that the projecting cutting blades can be replaced by other implements to suit any other function that is required to be performed on the internal surface of a pipe.

Two embodiments of the invention will now be described with reference to the accompanying drawings, in which.

Figure 1:
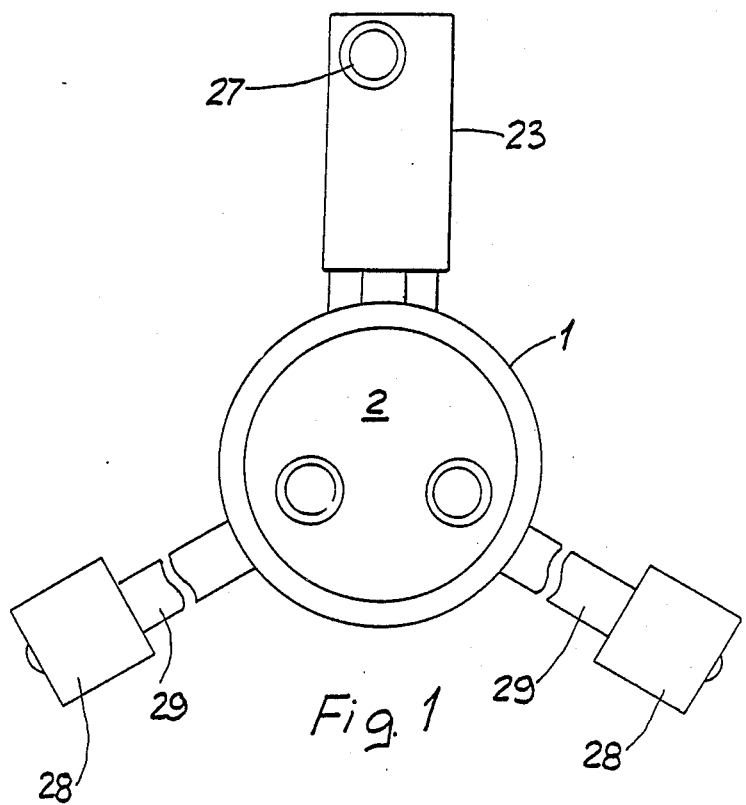
FIG. 1 is an end elevation of a cutting tool in accordance with the invention.
Figure 2:
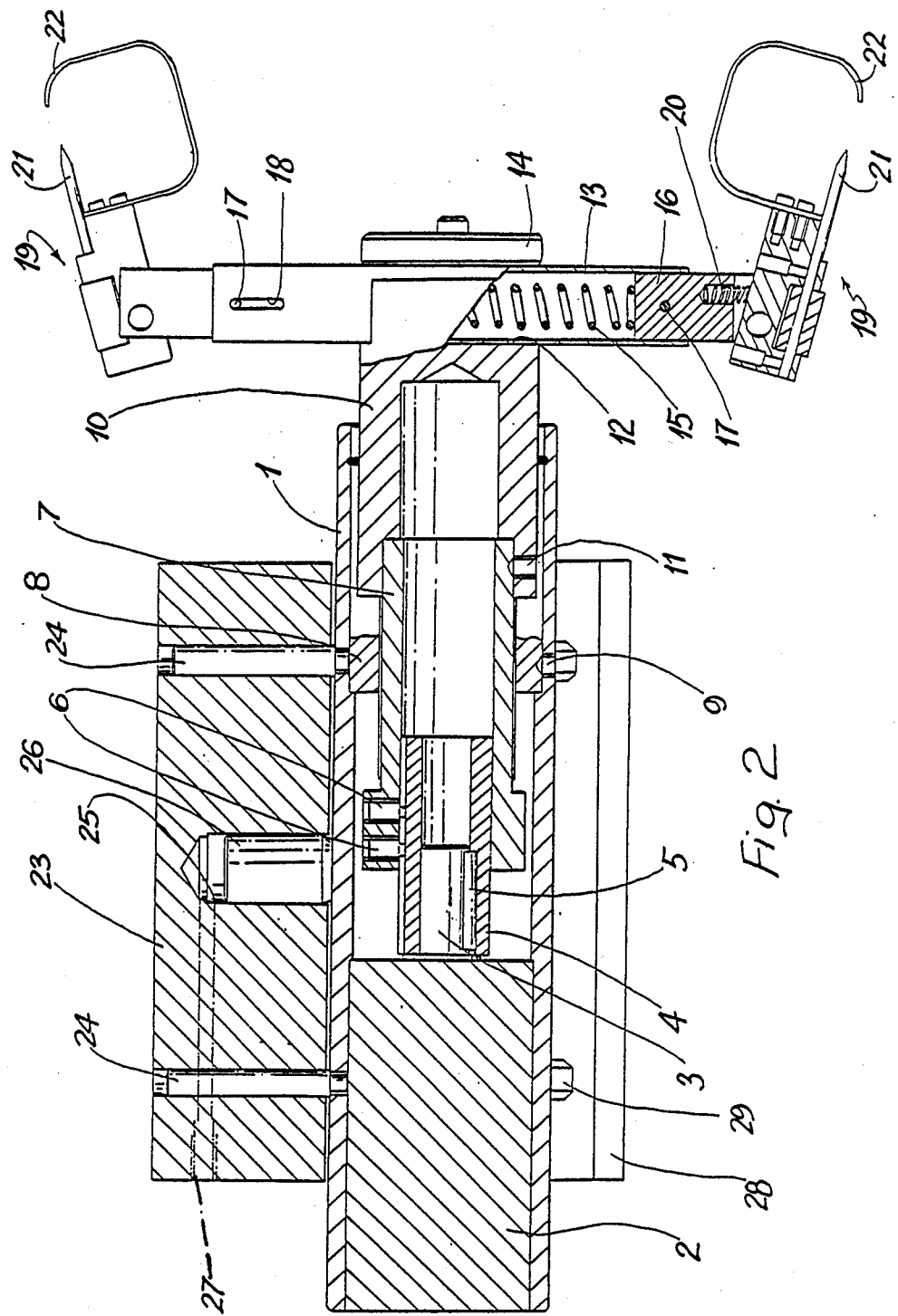
FIG. 2 is a sectional side elevation of the cutting tool of FIG. 1.

In FIGS. 1 and 2 a cutting tool for removing an internal bead at the joint between two pipe lengths of plastics material, has a cylindrical body 1, within which, at one end is a hydraulic motor 2, the drive shaft 3 of which is connected to a coupling sleeve 4, the coupling sleeve being slidably mounted on the drive shaft, and secured for rotation with the drive shaft by a key 5 located in corresponding keyways in the shaft and the coupling sleeve. The coupling sleeve 4 is connected by locating screws 6 to a feed screw 7 extending through a feed screw collar 8 located by screws 9 within the housing 1, the feed screw 7 extending to a cutter holder body 10, to which it is secured by screws 11, the cutter holder body 10 emerging from the end of the housing 1.

The exposed end of the cutter holder body has a transverse recess 12 in which locates a cutter support bar 13, and which is there secured by a clamping plate 14 engaging a threaded stem on the cutter holder body 10 that extends through a co-operating hole in the support bar 13. Within the support bar 13 is a spring 15 acting between support blocks 16 slidably mounted within the support bar, and held against ejection by locating pins 17 on the blocks engaging in slots 18 in the support bar. At the exposed ends of the support blocks, cutter assemblies 19 are provided, pivotally mounted and loaded in an outward direction by springs 20. Each cutter assembly has a cutter blade 21 and a collecting hook 22.

Externally of the body, the body 1 is provided with a clamping block 23 slidably mounted on pins 24 secured to the housing, there being within the clamping block a cylinder 25 containing a piston 26 that bears against the housing wall, and the cylinder having inlet ports 27 for hydraulic fluid. In equal spaced relationship round the housing, two skids 28 are provided, each mounted on a support member 29 to be at a distance from the housing to locate the axis of the housing substantially co-axial with the axis of a pipe.

Thus, with the cutter assemblies pivoted inwardly, the housing can be inserted into a pipe length, and can be slid along the pipe length the known distance to the position of a weld bead at the junction with the next pipe length. On reaching the weld bead, the collecting hook rides over the bead to locate the bead in the opening to the hook, and locate the cutter blade edge at the junction of the weld bead and the pipe wall. Hydraulic fluid is then supplied to the clamping block 23 to drive the clamping block away from the housing, and into contact with the pipe wall, to provide the positive securing of the housing in its required location.

The hydraulic motor is then activated to rotate the feed screw 7 and hence the cutter support bar, the feed screw progressing through the screw collar 8, to progress the cutter blades 21 along the pipe as they are rotated around the pipe wall. As a result, the internal weld bead is cut cleanly from the pipe wall and remains intact. Once cutting has been completed, the cut bead is gathered by the collecting hooks and is removed from within the pipe as the housing is withdrawn.

Figure 3:
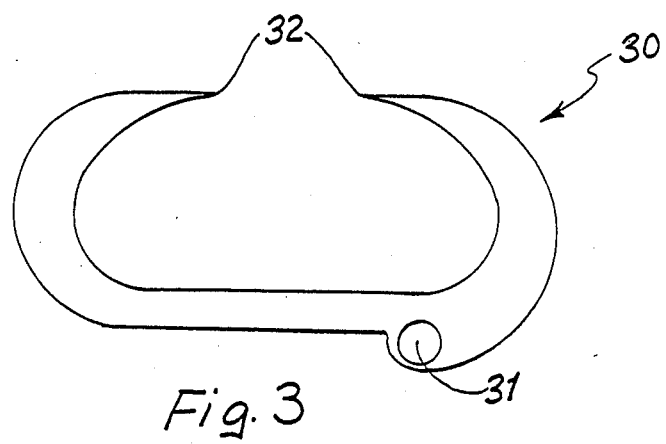
FIG. 3 is a side elevation of an alternative cutter of the invention.

In the alternative construction shown in FIG. 3, in place of a cutter assembly with a cutter blade and collecting hook, a forward and reverse cutter 30 is shown having a pivot point 31 for connecting to the support blocks 16 of the cutter support bar 13 of FIG. 2. In this embodiment, the cutter 30 has two opposed cutting edges 32 in spaced relation on a generally C-shaped blade member that serves the purpose of a bead collecting hook. With this embodiment, once the internal weld bead has been located between the two cutting edges, the hydraulic motor can be activated as described with reference to FIG. 2, or as circumstances may require, the hydraulic motor can be driven in the reverse direction to rotate the cutters and simultaneously draw them towards the housing, and when the opposite cutting edge of the blade cuts through the junction of the weld bead and the pipe wall. In either circumstance, once the weld bead has been severed, it is picked up by the cutter blade 30 for removal from within the pipe along with the housing.

I claim:

1. A plastics pipe internal joint bead cutting tool comprising a body member, adjustable support means on the body member to locate the body member within the pipe, a motor associated with the body member, a drive shaft extending from the motor, a feed screw means slidably mounted on the shaft, the feed screw means engaging a threaded bore in a drive screw means located in the body member, bead cutter means removably secured to the end of the feed screw means, and said bead cutter means being formed as both a bead cutter and a bead extraction means enable intact extraction of a cut bead within the pipe along with the cutting tool.

2. A cutting tool as in claim 1, wherein the motor drive shaft engages in a bore in the feed screw means, key and keyway means being employed to provide for the positive driving of the feed screw means by the motor drive shaft whilst permitting the feed screw means to slide along the motor drive shaft.

3. A cutting tool as in claim 1, wherein three support means are provided around the body member to locate the body member centrally of the pipe, at least one of which is adjustable.

4. A cutting tool as in claim 3, wherein one support means is hydraulically actuated and the two other support means being such as to locate the body centrally of the pipe.

5. A cutting tool as in claim 1, wherein the bead cutter means is in the form of a bar removably secured transversely of the end of the feed screw means with a bead cutter attached at at least one end of the transverse bar.

6. A cutting tool as in claim 5, wherein the at least one bead cutter is resiliently mounted at the at least one end of the transverse bar.

7. A cutting tool as in claim 6, wherein the at least one bead cutter is pivotally mounted.

8. A plastic pipe internal joint bead cutting tool comprising a body member, adjustable support means on the body member to locate the body member within the pipe, a motor associated with the body member, a drive shaft extending from the motor, a feed screw means slidably mounted on the shaft, the feed screw means engaging a threaded bore in a drive screw means located in the body member, bead cutter means removably secured to the end of the feed screw means, and there being means to engage a cut bead and enable its intact extraction from within the pipe along with the cutting tool, wherein the bead cutter means is formed as a generally C-shaped member, the edges of which are constructed as bead cutters to enable the bead to be cut by both a forward and a reverse drive from the motor, the cut bead being engagable in the C-shaped member to enable its extraction from within the pipe.

* * * * *